(12) United States Patent
Horn

(10) Patent No.: US 8,987,270 B2
(45) Date of Patent: *Mar. 24, 2015

(54) FORMULATIONS OF SELECTIVE ALPHA-2 AGONISTS AND METHODS OF USE THEREOF

(75) Inventor: Gerald Horn, Deerfield, IL (US)

(73) Assignee: Eye Therapies LLC, Dana Point, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 13/606,637

(22) Filed: Sep. 7, 2012

(65) Prior Publication Data

US 2012/0328687 A1 Dec. 27, 2012

Related U.S. Application Data

(63) Continuation-in-part of application No. 12/460,942, filed on Jul. 27, 2009, now Pat. No. 8,338,421, and a continuation-in-part of application No. 12/928,749, filed on Dec. 17, 2010, now Pat. No. 8,765,758.

(51) Int. Cl.
*A61K 31/498* (2006.01)
*C07D 241/42* (2006.01)
*A61K 9/00* (2006.01)
*A61K 9/08* (2006.01)
*A61K 45/06* (2006.01)
*A61K 31/00* (2006.01)

(52) U.S. Cl.
CPC ............... *A61K 9/0048* (2013.01); *A61K 9/08* (2013.01); *A61K 31/498* (2013.01); *A61K 45/06* (2013.01); *A61K 31/00* (2013.01)
USPC .......................... 514/249; 514/250; 424/429

(58) Field of Classification Search
CPC ........................... A61K 31/498; C07D 241/42
USPC .................................. 514/249, 250; 424/429
See application file for complete search history.

(56) References Cited

U.S. PATENT DOCUMENTS

| | | | |
|---|---|---|---|
| 4,663,340 A | 5/1987 | Najer et al. | |
| 5,021,416 A | 6/1991 | Gluchowski | |
| 5,300,504 A | 4/1994 | Gluchowski | |
| 5,304,569 A | 4/1994 | Lammintausta et al. | |
| 5,424,078 A | 6/1995 | Dziabo et al. | |
| 5,561,132 A | 10/1996 | Burke et al. | |
| 5,605,911 A | 2/1997 | Olney et al. | |
| 5,677,321 A | 10/1997 | Jeon et al. | |
| 5,712,301 A | 1/1998 | Heinonen et al. | |
| 5,756,503 A | 5/1998 | Burke et al. | |
| 5,804,587 A | 9/1998 | Cupps et al. | |
| 5,885,550 A * | 3/1999 | Vallier .................. | 424/10.32 |
| 5,914,342 A | 6/1999 | Maurer et al. | |
| 5,916,900 A | 6/1999 | Cupps et al. | |
| 5,948,804 A | 9/1999 | Jeon et al. | |
| 5,965,595 A | 10/1999 | Maurer et al. | |
| 6,040,451 A | 3/2000 | Jeon et al. | |
| 6,087,361 A | 7/2000 | Munk et al. | |
| 6,110,952 A | 8/2000 | Henry et al. | |
| 6,117,871 A | 9/2000 | Maurer et al. | |
| 6,159,998 A | 12/2000 | Jeon et al. | |
| 6,162,818 A | 12/2000 | Henry et al. | |
| 6,194,415 B1 | 2/2001 | Wheeler et al. | |
| 6,242,442 B1 * | 6/2001 | Dean et al. .................. | 514/222.8 |
| 6,248,741 B1 | 6/2001 | Wheeler et al. | |
| 6,465,464 B2 | 10/2002 | Wheeler et al. | |
| 6,534,048 B1 | 3/2003 | Borgman | |
| 6,562,855 B1 | 5/2003 | Franks et al. | |
| 6,562,873 B2 | 5/2003 | Olejnik et al. | |
| 6,627,210 B2 | 9/2003 | Olejnik et al. | |
| 6,641,834 B2 | 11/2003 | Olejnik et al. | |
| 6,653,354 B2 | 11/2003 | Franks et al. | |
| 6,673,337 B2 | 1/2004 | Olejnik et al. | |
| 6,730,065 B1 | 5/2004 | Horn | |
| 6,916,811 B2 | 7/2005 | Boyle et al. | |
| 6,982,079 B2 | 1/2006 | Huth | |
| 7,030,149 B2 | 4/2006 | Chang et al. | |
| 7,309,706 B2 | 12/2007 | Rupp et al. | |

(Continued)

FOREIGN PATENT DOCUMENTS

WO 2009022096 A1 2/2009
WO 2009124755 A1 4/2009

OTHER PUBLICATIONS

Mechanism of decongestant activity of x2-adrenoceptor agnosits, Corboz M.R. et al., Pulmonary Pharmacology & Therapeutics 21 (2008) 449-454.
Alpha-adrenoceptor agonistic activity of oxymetazoline and xylometazoline, Haenisch B. et al., Fundam Clin Pharmacol. Dec. 17, 2009.
An Evaluation of Nasal Response Following Different Treatment Regimes of . . . , Morris S. et al., American Journal Rhinology, vol. 11, No. 2, Mar-Apr. 1997, pp. 109-115(.
Pharmacological Characterization of Postjunctional a-Adrenoceptors in . . . , Corboz M.R. et al., American Jour of Rhinology, vol. 19, No. 5, Sep.-Oct. 2005, pp. 495-502.
Postjuntional a2-adrenoceptors in blood ve3ssels of human nasal mucosa, Ichimura K. et al., Arch Otorhinolaryngol (1988) 245:127-131.

(Continued)

*Primary Examiner* — Sreeni Padmanabhan
*Assistant Examiner* — Sahar Javanmard
(74) *Attorney, Agent, or Firm* — Wood, Phillips, Katz, Clark & Mortimer

(57) ABSTRACT

The invention provides compositions and methods utilizing low concentrations of selective α-2 adrenergic receptor agonists, preferably, brimonidine. The invention provides contact lens solutions and methods of using these solutions for presoaking contact lenses to achieve reduction of redness and/or increase in whitening of eyes. The invention also provides compositions including a selective α-2 adrenergic receptor agonist in a combination with an ocular medical device, including but not limited to a bandage lens. The invention also provides combination compositions including a selective α-2 adrenergic receptor agonist and another active agent for the treatment of an ocular condition, including but not limited to glaucoma and/or a condition associated with eye redness.

2 Claims, 1 Drawing Sheet

(56) References Cited

U.S. PATENT DOCUMENTS

| | | | |
|---|---|---|---|
| 7,589,057 | B2 | 9/2009 | Chang et al. |
| 7,678,829 | B2 | 3/2010 | Matier et al. |
| 2001/0049369 | A1 | 12/2001 | Jablonski et al. |
| 2002/0156076 | A1 | 10/2002 | Chow et al. |
| 2002/0197300 | A1 | 12/2002 | Schultz et al. |
| 2003/0181354 | A1 | 9/2003 | Abdulrazik |
| 2003/0229088 | A1 | 12/2003 | Donello et al. |
| 2004/0132824 | A1 | 7/2004 | Donello et al. |
| 2004/0266776 | A1 | 12/2004 | Gil et al. |
| 2005/0020600 | A1 | 1/2005 | Scherer |
| 2005/0026924 | A1 | 2/2005 | Graham et al. |
| 2005/0058696 | A1 | 3/2005 | Donello et al. |
| 2005/0059664 | A1 | 3/2005 | Gil et al. |
| 2005/0244468 | A1 | 11/2005 | Huang et al. |
| 2005/0244474 | A1 | 11/2005 | Huang et al. |
| 2006/0264442 | A1 | 11/2006 | Ruiz et al. |
| 2007/0031472 | A1 | 2/2007 | Huang et al. |
| 2007/0203085 | A1 | 8/2007 | Lang |
| 2008/0020076 | A1 | 1/2008 | Jhamandas et al. |
| 2008/0131483 | A1 | 6/2008 | Abdulrazik |
| 2008/0131485 | A1 | 6/2008 | Huang et al. |
| 2008/0207627 | A1 | 8/2008 | Gil et al. |
| 2008/0207628 | A1 | 8/2008 | Gil et al. |
| 2008/0233053 | A1 | 9/2008 | Gross et al. |
| 2009/0176843 | A1 | 7/2009 | Bhat et al. |
| 2009/0220611 | A1 | 9/2009 | Castan et al. |
| 2010/0028266 | A1 | 2/2010 | Horn |
| 2010/0029659 | A1 | 2/2010 | Horn |
| 2010/0029661 | A1 | 2/2010 | Horn |
| 2010/0029662 | A1 | 2/2010 | Horn |
| 2010/0029663 | A1 | 2/2010 | Horn |

OTHER PUBLICATIONS

Long-term use of oxy- and xylometazoline nasal sprays induces rebound swelling, tolerance, and nasal hyperreactivity, Graf P., Rhinology 1996, 34(1):9-13.
Alpha 1-receptors at pre-capillary resistance vessels of the human nasal mucosa, Johannssen V et al., Rhinology 1997; 35(4):161-65.
Correspondence A Propos De L'article: <<Traitement Des Glaucomes Par La Brimonidine>>, M. Detry-Morel Et C. Dutrieux< J Fr Ophtalmol.2001; 24(7): 748-9.
Potent a2A-Adrenoceptor-Mediated Vacoconstriction by Brimonidine in Porcine Ciliary Arteries, Anna Wikberg-Matsson, et al., IOVS, 2001, vol. 42, No. 9, 2049-55.
Medical Management of Chronic Rhinosinusitus—Jean P. Fong, MD, Matthew Ryan, MD (May 2006).
Prevent Drugs from Going Missing in Action—Mark B. Abelson, MD, and Sarah A. Rosner MPH; Review of Opthalmology; www.revophth.com/index.asp?page1_357.htm.
Interactions Between CA2+ and H+ and Functional Consequences in Vascular Smooth Muscle—C. Austin and S. Wray, Journ. of Amer. Heart Association (Circ. Res. 2000; 86:355-363).
A Useful New Topical Treatment for Glaucoma and Ocular Hypertension—Drug Ther Perspect 13(1):1-4, 1999.
Briminodine in the Treatment for Glaucoma and Ocular Hypertension—Drug Ther. Perspect. 13(1):1-4, 1999.
Silent Bedpartners—Nancy A. Collop, Chest 2002; 122, 1111-1112.
Traitment Des Glaucomes Par La Briminodine (Alphagan 0.2%)—M. Detry-Morel, C. Dutrieux, J. Fr. Opthamol., 2000; 23, 8, 763-768.
Vasopressin-Induced Vasoconstriction; Two Concentration-Dependen Signaling Pathways—Kyle K. Henderson and Kenneth L. Bryon, J. Appl. Physiol. 102: 1402-1409, 2007.
The Effect of Correction of Sleep-Disordered Breathing on Bp in Untreated Hypertension—K. Mae Hla, J.B. Skatrud, L. Finn, M. Palta and T. Young, Chest 2002:122 1125-1135.
Myogenic Tone and Reactivity of the Rat Opthalmic Artery—Y.P.R. Jarajapu, M.B. Grant, and H.J. Knot Invest. Opth. & Visual Science, Jan. 2004, vol. 45, No. 1.
Correspondence a Propos De L'article: <<Traitement Des Clauclomes Par La Brimonidine>>, M. Detry-Morel et al., J. Fr. Opthamol. 2000; 23(8): 763-8.

Prospective Study of the Association Between Sleep-Disordered Breathing and Hypertension—P. Peppard, et. al., The New England J. of Med, vol. 342, No. 19:1378:1384 (2000).
Catecholemnines and Sympathomimetic Drugs—Goodman & Gilman's Pharmacology, Ch. 10; www.accessmedicine.com/popup.aspx?a1D-936314&pring=yes_chapter.
Rhinitis Medicamentosa—JT Ramey, E Bailen, RF LOckey, J. Investig. Allergol. Clin. Immunol. 2006; vol. 16(3); 148-155.
Characterization of three inhibitors of endothelial nitric oxide synthase in vitro and in vivo—DD> Rees, et al., br. J. Pharmacol. (1990) 101, 746-752.
Inhibition of a-adrenergic vasoconstriction in exercising human thigh muscles—D. Walter Wray, et al., J. Physiol. 555, 2 pp. 545-564 (2003).
Dexmedetomidine Enhances the Local Anesthetic Action of Lidocaine via . . . Tatsushi Yoshitomi DDS et al., Anesth. Analg. 2008I 107:96-101.
Adding Dexmedetomidine to Lidocaines for Intravenous Regional Anesthesia, Dilek Memis, MS et. al, Anesth. Analg. 2004:98:835-40.
U.S. Appl. No. 09/948,001, filed Sep. 6, 2001, Chow et al.
Gilsbach et al., Genetic dissection of a2-adrenoceptor functions in adrenergic versus nonadrenergic cells, Molecular Phar 2009, 75(5), p. 1160-1170.
Sato et al., In Silico Functional Profiling of Small Molecules and Its Applications, Journal of Medical Chemistry 2008, 51(24), 7705-7716 (Abstract).
Lehtimaeki et al., In vitro and in vivo profiling of fadolmidine, a novel potent a2-adrenoceptor agonist with local mode of action, European Journal of Pharmacology 2008, 599(1-3), 65-71 (Abstract).
Verbruggen et al., The effect of intravenous medetomidine on pupil size and intraocular pressure in normotensive dogs, Veterinary Quarterly 2000, 22(3), 179-180 (Abstract).
Wong et al., Design and synthesis of alpha2 adrenoceptor agonists, Book of Abstracts, 213th ACS National Meeting, San Francisco, Apr. 13-17, 1997, MEDI-023, American Chemical Society: Washington, D.C., (Abstract).
Ogidigben et al., Comparative effects of alpha-2 and DA-2 agonists on intraocular pressure in pigmented and nonpigmented rabbits, Journal of Ocular Pharmacology 1993, 9(3), 187-99 (Abstract).
MacDonald et al., Comparison of the cardiovascular effects of the a2-adrenoceptor agonist, dexmedetomidine, in rats and rabbits, Drug Development Research 1993, 28(4), 473-477 (Abstract).
Jin et al., Ocular hypotensive effects of medetomidine and its analogs, Journal of Ocular Pharmacology 1991, 7(4) 285-296 (Abstract).
Laengle et al., GLC756 decreases TNF-alpha via an alpha2 and beta2 adrenoceptor related mechanism, Experimental eye research, Nov. 2006, 83(5), 1246-1251 (Abstract).
Stamer et al., Cultured human trabecular meshwork cells express functional alpha 2A adrenergic receptors, Investigative ophthalmology & visual science Nov. 1996, 37(12), 2426-2433 (Abstract).
Pate et al., Ophthalmic arachidonylethanolamide decreases intraocular pressure in normotensive rabbits, Current eyer research Sep. 1995, 14(9), 791-797 (Abstract).
Jin et al., Ocular a2-receptor subclasses and antiglaucoma efficacy, Journal of Ocular Pharmacology, 1994, 10(1), 359-369 (Abstract).
Potter et al., Review: Alpha2 and DA2 agonists as antiglaucoma agents: Comparative pharmacology and clinical potential, Journal of Ocular Pharmacology, 1990, 6(3), 251-257 (Abstract).
Kost et al., Procedural Sedation and Analgesia in the Pediatric Emergency Department: A Review of Sedative Pharmacology, Clinical Pediatric Emergency Medicine, Dec. 2010, 11(4), 233-243 (Abstract).
Penha et al., Retinal and ocular toxicity in ocular application of drugs and chemicals—Part I: Animal models and toxicity assays, Ophthalmic Research, Jul. 2010, 44(2), 82-104 (Abstract).
Mowafi et al., Effect of dexmedetomidine premedication on the intraocular pressure changes after succinylcholine and intubation, British Journal of Anaesthesia, Apr. 2008, 100(4), 485-489.
Mowafi et al., Remifentanil obtunds intraocular pressure rises associated with suxamethonium, British Journal of Anaesthesia, Sep. 2008, 101(3), 432-433.
Bielory, Chirality in ocular agents, Current Opinion in Allergy and Clinical Immunology, Oct. 2007, 7(5), 418-423 (Abstract).

(56) References Cited

OTHER PUBLICATIONS

Freeman, Hypoxic-ischaemic brain injury (HIBI) after cardiopulmonary arrest, Current Anaesthesia and Critical Care, 2007, 18(5-6), 261-276 (Abstract).

Crassous et al., Interest of a2-adrenergic agonists and antagonists in clinical practice: Background, facts and perspectives, Current Topics in Medicinal Chemistry, Jan. 2007, 7(2), 187-194 (Abstract).

Gentili et al., Agonists and antagonists targeting the different a2-adrenoceptor subtypes, Current Topics in Medicinal Chemistry, Jan. 2007, 7(2), 163-186 (Abstract).

Weber et al., Neuroprotective effects of a2-adrenergic receptor agonists, Drug News and Perspectives, Apr. 2007, 20 (3), 149-154 (Abstract).

Loots, Agents for sedation in ophthalmic surgery: A review of the pharmacodynamics and clinical applications, Current Anaesthesia and Critical Care, 2006, 17(3-4), 179-190 (Abstract).

Robertson, Standing sedation and pain management for ophthalmic patients, Veterinary Clinics of North America—Equine Practice, Aug. 2004, 20(2), 485-497 (Abstract).

Ruffolo et al., a-Adrenoceptors, Pharmacology and Therapeutics, 1994, 61(1-2), 1-64 (Abstract).

Tripathi et al., Role of receptors in the trabecular meshwork of the eye as targeted to the development of antiglacoma therapy, Drug Development Research, 1992, 27(3), 1991-228 (Abstract).

Georgiou et al., Changes in NMDA receptor contribution to synaptic transmission in the brain in a rat model of glaucoma, Neurobiology of Disease, Sep. 2010, 39(3), 344-351 (Abstract).

Schoewald et al., Relationship between Steroid Permeability across Excised Rabbit Cornea and Octanol-Water Partition Coefficients, Journal of Pharmaceutical Scienses, Jun. 1978, 67(6), 786-788.

Chang et al., Improved Corneal Penetration of Timolol by Prodrugs as a Means to Reduce Systemic Drug Load, 1987, 28(3), 487-491.

Li et al., A Study of the Relationship between Cornea Permeability and Eye Irritation Using Membrane-Interaction QSAR Analysis, Toxicological Sciences, 2005, 88(2), 434-446.

Forster, et al., Adrenergic Alpha1, and Alpha2 Binding Sites are Present in Bovine Retinal Blood Vessels, Investigative Ophthalmology & Visual Science, 1987, 28(11), 1741-1746.

Donello et al., a2-Adrenoceptor Agonists Inhibit Vitreal Glutamate and Aspartate Accumulation and Preserve Retinal Function after Transient Ischemia, Journal of Pharmacology and Experimental Therapeutics, 2011, 296(1), 216-223.

Akasu et al., Reduction of the N-Type Calcuium Current by Noradrenaline in Neurones of Rabbit Vesical Parasympathetic Ganglia, Journal of Physiology, 1990, 426, 439-452.

Trendelenburg et al., a2-Adrenoceptor-mediated inhibition of cultured sympathetic neurons: changes in a2A/D-adrenoceptor-deficient mice, Naunyn-Schmiedeberg's Arch Pharmacology, 2011, 363, 110-119.

Dong et al., a2 Adrenergic Modulation of NMDA Receptor Function as a Major Mechanism of RGC Protection in Experimental Glaucoma and Retinal Excitotoxicity, Investigative Ophthalmology & Visual Science, Oct. 2008, 49(10), 4515-4522.

Saylor et al., Experimental and Clinical Evidence for Brimonidine as an Optic Nerve and REtinal Neuroprotective Agent, Arch Ophthalmol, Apr. 2009, 127(4), 402-406.

Shirasaka et al., Activation of a G Protein-coupled Inwardly Rectifying K+ Current and Suppression of Ih Contribute to Dexmedetomidine-induced Inhibition of Rat Hypothalamic Paraventricular Nucleus Neurons, Anesthesiology, 2007, 107, 605-615.

Rosa et al., Brimonidine evokes hetrogenous vasomotor response of retinal arterioles: diminished nitric oxide-mediated vasodilation when size goes small, Am J Physiol Heart Cir Physiol 2006, 291, H231-H238.

Wirostoko et al., The Vascular Theory in Glaucoma, Glaucoma Today, Apr. 2009, 25-27.

Huang et al., The two sides of cytokine signaling and glaucomatous optic neuropathy, j ocul biol dis inform, 2009, 2, 98-103.

Hamasaki et al., Dual a2-Adrenergic Agonist and al-Adrenergic Antagonist Actions of Dexmedetomidine on Human Isolated Endothelium-Denuded Gastroepiploic Arteries, Anesth Analg, 2002, 94, 1434-1440.

Paris et al., The Anesthetic Effects of Etomidate: Species-Specific Interaction with a2-Adrenoceptors, Anesth Analg. 2007, 105(6), 1644-1649.

Pertovaara, Antinociceptive Properties of Fadolmidine (MPV-24-26), a Novel a2-Adrenoceptor Agonist, CNS Drug Reviews, 2004, 10(2), 117-126.

Niemi et al., Synthesis, hydrolysis, and intraocular pressure lowering effects of fadolmidine prodrugs, International Journal of Pharmaceutics 2005, 29, 121-127.

Vaidyanathan S. et al., Fluticasone Reverses Oxymetazoline-induced Tachyphylaxis of Response and Rebound Congestion, American Journal of Respiratory and Critical Care Medicine vol. 182, 19-24, 2010.

AFT Pharmaceuticals Ltd., Brimonidine AFT. 2005; p. 1, para 2-3, 5 http://www.medsafe.govt.nz/Profs/Datasheet/b/Brimonidine-AFTeyedrops.pdf.

\* cited by examiner

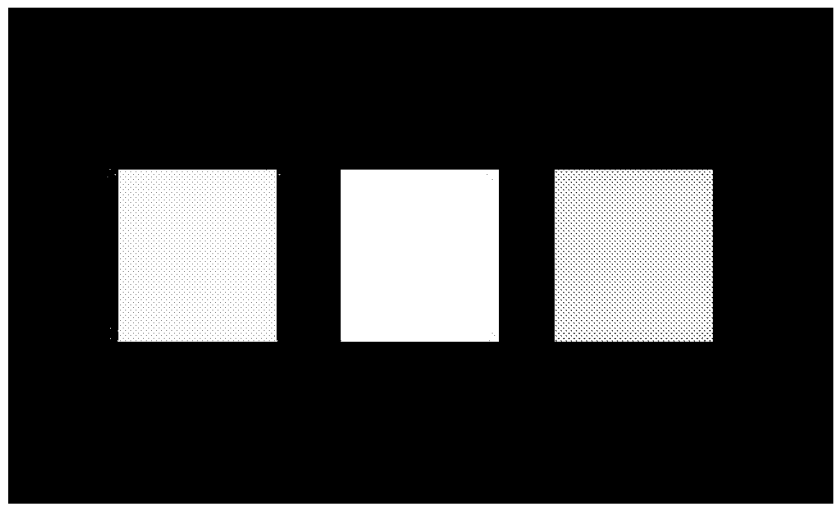

US 8,987,270 B2

FORMULATIONS OF SELECTIVE ALPHA-2 AGONISTS AND METHODS OF USE THEREOF

BACKGROUND OF THE INVENTION

Eye redness and eye whitening are polar opposites on the spectrum of societal perceptions of general health, similar to the perceptions associated with yellow teeth versus white teeth. Those with red eyes or yellow teeth are often perceived as experiencing poor health, poor hygiene, and/or otherwise participating in unsavory habits such as binge drinking, excessive alcohol use, recent drug use, excessive use of cigarettes, or all of the above.

Contact lens-induced hyperemia (redness) is a common problem associated with contact lens wear. Soft contact lenses, regardless of material, including but not limited to hydrogels, and regardless of duration of wear are associated with a significant redness that occurs in a substantial percentage of patients with their routine use, even in the absence of infection or other serious consequences.

While one could potentially apply a drop to an eye to reduce redness, this approach has several drawbacks. First, many conventional drugs cause rebound hyperemia, resulting in more redness. Second, having to apply an eye drop is an extra undesirable step to have to take after insertion of a contact lens. It would be much simpler and easier if one could simply insert a contact lens that would reduce redness and also preferably increase whiteness. It would result in an improved visual appearance, potentially leading to greater personal esteem and compliance with daily lens wear.

It is also important that such a contact lens, while reducing common minor eye redness, still allow for an eye to become noticeably redder if it is experiencing a serious pathological condition, such as bacterial infiltrates or ulceration of the cornea, anterior inflammations of the eye, and/or posterior inflammations of the eye. This is important for diagnostic reasons so that those affected would know to seek immediate care. In other words, a contact lens developed to reduce causes of redness must preferably not mask more serious acute red eye conditions.

Unfortunately, no contact lens material or decongestant drug associated with contact lens insertion has been able to achieve eye whitening. It is therefore highly desirable to be able to insert a contact lens which would not only not make eyes redder, but preferably make eyes whiter.

Accordingly, there is a need for a contact lens that would achieve these results.

In addition, it is desirable to arrive at improved formulations and methods of treatment of various ocular conditions, including but not limited to glaucoma and/or conditions associated with eye redness.

SUMMARY OF THE PRESENT INVENTION

In one aspect, the present invention provides contact lens compositions and methods for achieving reduction of eye redness and/or cosmetic eye whitening, utilizing low concentrations of selective α-2 adrenergic receptor agonists.

In another aspect, the present invention provides compositions comprising a selective α-2 adrenergic receptor agonist in a combination with an ocular medical device, including but not limited to a bandage lens.

In yet another aspect, the present invention provides compositions comprising a combination of a selective α-2 adrenergic receptor agonist and another active agent for the treatment of an ocular condition, including but not limited to glaucoma and/or a condition associated with eye redness.

In some embodiments of the invention, the selective α-2 adrenergic receptor agonists have binding affinities ($K_i$) for α-2 over α-1 receptors of 500:1 or greater. In preferred embodiments of the invention, the selective α-2 adrenergic receptor agonists have $K_i$ for α-2 over α-1 receptors of 750:1 or greater, more preferably even more preferably 1000:1 or greater, and most preferably, 1500:1 or greater.

In addition, it has been discovered that less lipophilic α-2 agonists, such as brimonidine, have more profound redness reduction and whitening effect than other preferred embodiments that are more highly lipophilic, such as dexmedetomidine. Therefore, preferred embodiments of the invention, in addition to having high α-2: α-1 selectivity, also have a Log P value of <3.0, more preferably <2.0 and still more preferably <1.0.

In preferred embodiments of the invention, concentrations of the selective α-2 adrenergic receptor agonists are from about 0.0001% to about 0.05%; more preferably, from about 0.001% to about 0.025%; even more preferably, from about 0.01% to about 0.025%; and even more preferably, from about 0.01% to about 0.02% weight by volume of the composition.

The compositions and methods of the invention may be used to reduce redness in an eye and/or to whiten healthy eyes.

The reduction in redness and additional increase in whiteness can be measured on one of the following scales, such as the McMonnies/Chapman-Davies scale (MC-D); the Institute for Eye Research scale (IER, previously known as CCLRU scale); the Efron scale; and a validated bulbar redness scale (VBR) developed at the Centre for Contact Lens Research. (*The Use of Fractal Analysis and Photometry to Estimate the Accuracy of Bulbar Redness Grading Scales*, Marc M. Schulze et al, Investigative Ophthalmology and Visual Science, 2008; 49:1398-1406). Alternatively, the invention also describes a modified scale that can more accurately measure the reduction in redness and the additional increase in whiteness.

BRIEF DESCRIPTION OF THE FIGURES

FIG. 1 is a visual representation of three different shades of whiteness.

DETAILED DESCRIPTION OF THE INVENTION

Definitions

For purposes of the present invention, the terms below are defined as follows.

The term "low concentrations" refers to concentrations from between about 0.0001% to about 0.05%; more preferably, from about 0.001% to about 0.025%; even more preferably, from about 0.01% to about 0.025%; and even more preferably, from about 0.01% to about 0.02% weight by volume of the composition.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan™, and UK14304.

As used herein, the term "composition" is intended to encompass a product comprising the specified ingredients in the specified amounts, as well as any product which results, directly or indirectly, from a combination of the specified ingredients in the specified amounts.

Embodiments of the Invention

The presently claimed methods and compositions can increase whiteness of an eye several shades beyond the baseline of a particular eye. This increase in whiteness may be important for cosmetic or other reasons. A normal healthy eye has a certain baseline level of whiteness, which slightly varies from person to person. The reduced whiteness of the sclera is often viewed as cosmetically less desirable, and may be an indicator of fatigue, lack of sleep, lack of sobriety, drug use, emotional lability, and overall poor health. Whiter sclera is often viewed as more cosmetically desirable, associated with improved hygiene and/or health, and a cleaner, healthier lifestyle.

Not wishing to be bound to a specific theory, the present invention may accomplish this additional whitening through microvascular vasoconstriction of the vessels and, particularly, microvessels of the white layer of the eye (i.e., the sclera). In addition, compositions and methods of the present invention may affect vasoconstriction of overlying episcleral and/or conjunctival tissue microvessels which may also be involved in the whitening of an eye. This effect is believed to be similar to teeth whitening, where grading scale quantification includes improvement relative to an estimated baseline, where whitening beyond baseline is referred to as "bleaching."

It was surprisingly and unexpectedly found that selective alpha-2 (α-2) adrenergic receptor agonists (which are interchangeably referred to as "α-2 agonists" throughout the application) at sufficiently low concentrations can be used for preparing contact lens that reduce eye redness and/or provide cosmetic whitening of eyes with reduced or eliminated side effects.

The present invention also provides compositions comprising a selective α-2 adrenergic receptor agonist in a combination with an ocular medical device, including but not limited to a bandage lens.

The present invention also provides compositions comprising a combination of a selective α-2 adrenergic receptor agonist and another active agent for the treatment of an ocular condition, including but not limited to glaucoma and/or a condition associated with eye redness.

Suitable α-2 agonists have a high selectivity for α-2 vs α-1 receptors, i.e., a binding affinity ($K_i$) for α-2 over α-1 receptors of at least 500:1 or greater. In addition, in preferred embodiments of the invention, in addition to having high α-2:α-1 selectivity, α-2 agonists also have a Log P value of <3.0, more preferably <2.0 and still more preferably <1.0.

In the aspect of the invention relating to the contact lenses, the provided solutions, when allowed to soak into soft contact lenses via overnight soaking/storage and/or prepackaging in the case of daily wear disposables, reduce baseline eye redness and induce cosmetic whitening without masking or otherwise preventing the induction of redness from more serious pathogenic conditions associated with acute red eye.

Not wishing to be held to a particular theory, it is believed this effect occurs because the concentration range is surprisingly low and vasoconstriction effect is sufficiently small to only counteract minor irritants that cause vasodilation, but not more serious irritants. This is particularly surprising because cases of acute red eye are multifactorial in origin, and prior art makes no distinction as to the degree of vasodilation associated with red eye caused by allergens and/or routine contact lens wear versus pathologic conditions causing acute red eye.

This surprising finding allows one to arrive at a formulation sufficient to induce a decongestive effect, yet not sufficient to overcome the vasodilation induced by various cytokines whose release is triggered in conditions causing acute red eye.

It is a discovery of the present invention that solutions of extremely low concentrations of alpha-2 agonists, and in particular, brimonidine, may be applied to soft contact lenses for pre-packaged delivery (for daily wear disposables), or as a part of a contact lens storage and insertion solution for overnight soaking of non-disposable contact lens, resulting in the contact lenses being able to reduce eye redness and/or increase eye whiteness without masking or preventing acute eye redness with a more severe hyperemia.

In addition, it is well known that about 0.05% of contact lens wearers develop a microbial keratitis, or other microbial infections which can result in permanent vision loss. In some preferred embodiments, the provided solutions allow to reduce the risk of microbial infection, in particular, when these solutions contain brimonidine, borate and polyol.

It is also a discovery of the present invention that extreme low dose brimonidine at alkaline pH also unexpectedly results in pupil modulation in the form of reduced dilation to reduced light and may result in significant intraocular pressure reduction.

It is therefore a further object of the present invention to provide formulations which can: 1) provide cosmetic eye whitening; 2) enhance brimonidine surface decongestant action with greatly reduced or absent pupil modulation and/or intraocular pressure lowering; and 3) still allow acute redness conditions to induce vasodilation and pain for diagnostic purposes.

Selective α-2 Adrenergic Receptor Agonists Suitable for the Purposes of the Invention In some embodiments of the invention, selective α-2 adrenergic receptor agonists have binding affinities ($K_i$) for α-2 over α-1 receptors of 500:1 or greater. In preferred embodiments of the invention, selective α-2 adrenergic receptor agonists have $K_i$ for α-2 over α-1 receptors of 750:1 or greater, even more preferably 1000:1 or greater, and most preferably, 1500:1 or greater.

In preferred embodiments of the invention, concentrations of selective α-2 adrenergic receptor agonists are from about 0.0001% to about 0.05%; more preferably, from about 0.001% to about 0.025%; even more preferably, from about 0.01% to about 0.025%; and even more preferably, from about 0.01% to about 0.02% weight by volume of the composition.

Compositions and methods of the inventions encompass all isomeric forms of the described α-2 adrenergic receptor agonists, their racemic mixtures, enol forms, solvated and unsolvated forms, analogs, prodrugs, derivatives, including but not limited to esters and ethers, and pharmaceutically acceptable salts, including acid addition salts. Examples of suitable acids for salt formation are hydrochloric, sulfuric, phosphoric, acetic, citric, oxalic, malonic, salicylic, malic, fumaric, succinic, ascorbic, maleic, methanesulfonic, tartaric, and other mineral carboxylic acids well known to those in the art. The salts may be prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference).

As long as a particular isomer, salt, analog, prodrug or other derivative of a selective α-2 adrenergic receptor agonist functions as a highly selective α-2 agonist suitable for purposes of the invention, it may be used for the purposes of the present invention.

When choosing a particular α-2 adrenergic receptor agonist, one may take into account various considerations including blood brain permeability and any possible side effects and other systemic reactions.

In preferred embodiments of the invention, the selective α-2 adrenergic receptor is brimonidine or its salt. In a more preferred embodiment, the selective α-2 adrenergic receptor agonist is the tartrate salt of brimonidine.

Compositions and Methods of the Invention

In one embodiment, the invention provides a contact lens solution comprising a selective α-2 adrenergic receptor agonist having a binding affinity of 500 fold or greater for α-2 over α-1 adrenergic receptors, or a pharmaceutically acceptable salt thereof, wherein said α-2 adrenergic receptor agonist is present at a concentration from between about 0.001% to about 0.05% weight by volume.

The concentration of the selective α-2 adrenergic receptor agonist is preferably below the concentration at which α-1 adrenergic receptors are sufficiently activated to cause adverse ischemic vasoconstrictive consequences.

In a preferred embodiment, the contact lens solution comprises brimonidine at a concentration between about 0.001% and about 0.025% weight by volume.

The compositions comprising the selective α-2 adrenergic receptor agonist have a pH of between about 4.0 and about 6.5, more preferably between about 5.0 and about 6.0; and even more preferably between about 5.25 and 5.75.

In one embodiment, the invention provides a contact lens solution for daily wear disposable contact lenses, wherein the α-2 adrenergic receptor agonist is brimonidine at a concentration from between about 0.001% to about 0.05%, more preferably 0.005% to 0.025%, and still more preferably 0.010% to 0.15% weight by volume, wherein soaking the contact lens in the provided solution will allow the lens to reduce baseline hyperemia and induce cosmetic whitening upon insertion in an eye.

In a preferred embodiment, the contact lens solution further comprises one or more of the following:

boric acid, preferably at a concentration of less than 0.50%, and more preferably at about 0.30%;

borate salt, preferably at a concentration of less than 0.25%, and more preferably at about 0.13%;

dextrose, preferably at about 0.3%; and mannitol, glycerin or other polyol, preferably at a concentration of less than 4%, and more preferably at less than 1%.

These ingredients may help to provide simultaneous enhanced whitening and increased protection from infection.

Thus, in one embodiment, the invention provides a contact lens solution, wherein the α-2 adrenergic receptor agonist is brimonidine at a concentration from between about 0.01% to about 0.025% weight by volume, and wherein pH of said composition is between about 4.0 and about 6.5.

In another embodiment, the invention provides a contact lens storage solution, containing brimonidine, preferably at a concentration range of 0.001% to 0.005%, and more preferably at 0.010% to 0.015% weight by volume. Typically, such a storage medium may include preservatives, such as polyquaternium-1 and/or polyaminoprophyl buguanide.

In another embodiment, the invention provides a method of reducing eye redness the method comprising inserting a contact lens in the solution of the invention and then inserting this soaked contact lens into an eye.

The length of time for which the contact lens should be inserted in the provided solutions depends on a specific contact lens and a specific solution. It should be sufficient to pre-soak the contact lens enough so that it can provide the intended benefits. It is well within a skill of ordinary person in the art to determine the required time.

In another preferred embodiment, the compositions of the invention also comprise a solubility stabilizer which preferably contains an anionic component, such as peroxide class preservatives. The solubility stabilizer allows one to achieve greater penetration of lipophilic membranes, and more easily target the tunica media (muscle layer) of blood vessels. In a preferred embodiment, the solubility stabilizer comprises a stabilized oxychloro complex, chlorite, and sodium perborate.

In yet another preferred embodiment, the compositions of the present invention comprise nitrous oxide inhibitors. In a preferred embodiment, the nitrous oxide inhibitors are selected from the group consisting of L-NAME (L-$N^G$-Nitroarginine methyl ester), L-NIL (N-6-(1-Iminoethyl)-L-lysine dihydrochloride), L-NIO (N-5-(1-Iminoethyl)-L-ornithine dihydrochloride), and L-canavine, or combinations thereof. Preferably, concentration of the nitrous oxide inhibitors is between about 0.005% and about 0.5% weight by volume.

In one embodiment of the invention, the solutions may also include additional non-therapeutic components, which include, but are not limited to, preservatives, tonicity adjustors, buffers, pH adjustors, antioxidants, and water.

In another embodiment, the present invention provides compositions comprising a selective α-2 adrenergic receptor agonist in a combination with an ocular medical device, including but not limited to a bandage lens. Any ocular medical device may be used with the compositions of the invention.

In another embodiment, the present invention provides compositions comprising a combination of a selective α-2 adrenergic receptor agonist and one or more active agents for the treatment of an ocular condition, including but not limited to glaucoma and/or a condition associated with eye redness. Any active therapeutic agent for the treatment of any ocular condition may be used in the combination compositions.

Preservatives include, but are not limited to, benzalkonium chloride, chlorobutanol, thimerosal, phenylmercuric acetate, or phenylmercuric nitrate.

Tonicity adjustors include, but are not limited to, a salt such as sodium chloride, potassium chloride, mannitol or glycerin, or another pharmaceutically or ophthalmically acceptable tonicity adjustor.

Buffers and pH adjustors include, but are not limited to, acetate buffers, citrate buffers, phosphate buffers and borate buffers. It is understood that acids or bases can be used to adjust the pH of the composition as needed.

Antioxidants include, but are not limited to, sodium metabisulfite, sodium thiosulfate, acetylcysteine, butylated hydroxyanisole and butylated hydroxytoluene.

To make the solutions of the present invention, one can simply dilute, using methods known in the art, more concentrated solutions of selective α-2 agonists. The precise method of carrying out the dilutions is not critical. Any commonly used diluents, including preservatives described above in the application, suitable for topical solutions can be used.

FIG. 1 is a visual representation of three different shades of whiteness. The human eye has a limit to its ability to discriminate shades of whiteness change. The central square is set to RGB (255 255 255). The RGB color model is an additive color model in which red, green, and blue light are added together in various ways to reproduce a broad array of colors. A color in the RGB color model is described by indicating how much of each of the red, green, and blue is included. The color is expressed as an RGB triplet (rgb), each component of which can vary from zero to a defined maximum value. If all the components are at zero, the result is black; if all are at maximum, the result is the fully saturated white. RGB (255 255 255) represents the fully saturated white.

In the right square, the whiteness has been reduced by 5, based on a 1 to 100 blackness scale, where the background is 100. On the square to the left, the whiteness has been reduced by 15. The shade differential resulting from reduction by 5 is just above the threshold increment of difference in whitening detectable by most humans with normal healthy eyes.

The following Examples are provided solely for illustrative purposes and are not meant to limit the invention in any way.

EXAMPLES

Examples below describe some of the preferred compositions of the invention.

Example 1

Daily Disposable Lens, Preservative Free Storage Solution, Cosmesis Only

Brimonidine at a concentration of 0.005%-0.035%, preferably 0.075%-0.020%, and even more preferably at 0.01% to 0.015% weight by volume;
NaCl 0.50-0.90%;
Glycerin 0.3%;
optionally, contact lens safe preservatives including but not limited to peroxychloro and polyquaternium ammonium derivative, such as PQ-1; and
pH 4.0-6.5, more preferably 5.5-6.5, still more preferably 5.75-6.0.

Example 2

Daily Disposable Lens, Preservative Free or Contact Lens Preservative Safe Solution, Cosmesis and Antimicrobial Effect Brimonidine at a concentration of 0.005%-0.035%, preferably 0.075%-0.020%, and even more preferably at 0.01% to 0.015% weight by volume;
Boric acid 1.2%;
NaBorateDecahydrate 0.12%;
KCl 0.25%;
Dextrose 0.05% (or substitute equal tonicity mannitol, glycerin, other polyol); and
pH 5.0-6.5, preferably 6.0-6.5.

Example 3

Daily Disposable Lens, Preservative Free or Contact Lens Preservative Safe Solution, Cosmesis Pupil Modulation, with or without Antimicrobial Formulation Brimonidine at a concentration of 0.015%-0.040%, preferably 0.020% to 0.035%, and even more preferably at 0.025% to 0.030% weight by volume;
Buffer, borate-boric acid preferred;
NaCl 0.50% to 0.90%;
Glycerin 0.30%; and
pH 5.0-6.5.

What is claimed is:

1. A method of reducing eye redness, wherein said method consists essentially of inserting a contact lens in a solution consisting essentially of brimonidine or a pharmaceutically acceptable salt thereof, wherein said brimonidine is present at a concentration from between about 0.001% to about 0.05% weight by volume, and wherein said solution has a pH of between about 4.0 and about 6.5, and then inserting said contact lens into an eye.

2. The method of claim 1, wherein said brimonidine is at a concentration from between about 0.01% to about 0.025% weight by volume.

* * * * *